United States Patent [19]

Namiki et al.

[11] Patent Number: 5,747,493
[45] Date of Patent: May 5, 1998

[54] DOPAMINE RE-UPTAKE INHIBITOR

[75] Inventors: Takayuki Namiki; Toshihiro Morimoto; Kenichi Kishii; Nobuyuki Kawakatsu; Makoto Kimura; Kyoko Yamasaki; Mariko Onoda; Yuji Yoshiko; Kazunori Harada; Masayuki Yanagi; Takeshi Yamamoto; Masato Inazu; Masaki Mitani, all of Yokohama, Japan

[73] Assignee: Pola Chemical Industries, Inc., Shizuoka, Japan

[21] Appl. No.: 557,167

[22] PCT Filed: Apr. 28, 1994

[86] PCT No.: PCT/JP94/00728

§ 371 Date: Dec. 21, 1995

§ 102(e) Date: Dec. 21, 1995

[87] PCT Pub. No.: WO95/00149

PCT Pub. Date: Jan. 5, 1995

[30] Foreign Application Priority Data

Jun. 25, 1993 [JP] Japan ................. 5-155564

[51] Int. Cl.$^6$ ................. A61K 31/495
[52] U.S. Cl. ................. 514/255
[58] Field of Search .............. 514/255; 544/396, 544/360

[56] References Cited

FOREIGN PATENT DOCUMENTS

| A-53-82789 | 7/1978 | Japan . |
| A-61-236764 | 10/1986 | Japan . |
| A-1-153685 | 6/1989 | Japan . |
| A-3-7257 | 1/1991 | Japan . |
| A-56-138170 | 10/1991 | Japan . |
| WO-A-92 5165 | 4/1992 | WIPO . |

*Primary Examiner*—Phyllis G. Spivack
*Attorney, Agent, or Firm*—Bacon & Thomas

[57] ABSTRACT

A method for inhibiting dopamine re-uptake and treating Parkinson's disease is disclosed comprising administering a compound represented by formula (1) or a physiologically acceptable salt thereof as the active ingredient:

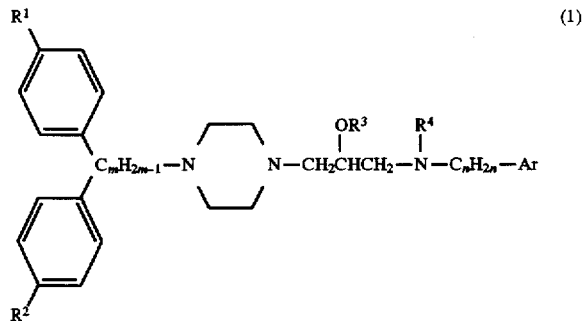

wherein $R^1$ and $R^2$ represent each hydrogen or halogen, $R^3$ represents hydrogen, alkyl or acyl, $R^4$ represents hydrogen, alkyl, acyl, alkylsulfonyl or optionally esterified carboxyl, Ar represents optionally substituted phenyl or nitrogenous monocyclic heteroaromatic group, m represents a number of 1 to 5, and n represents a number of 0 to 5.

10 Claims, No Drawings

DOPAMINE RE-UPTAKE INHIBITOR

The present application is a 371 of PCT/JP94/00728, filed Apr. 28, 1994.

1. Technical Field

The present invention relates to a dopamine re-uptake inhibitor, which is safe and high in efficacy, and a therapeutic agent for Parkinson's syndrome.

2. Background Art

Dopamine (hereinafter referred to as DA) is one of principal neurotransmitters having various physiological functions in central and peripheral nervous systems. The central dopaminergic has been known to play many roles in the motor function in an extrapyramidal system, the emotional control in a limbic system and the secretion of hormones in a pituitary system. Therefore, DA deficiency and decrease in the dopaminergic nerve activity form the cause of critical diseases.

For example, Parkinson's syndrome is a disease mainly showing a symptom that involuntary labile movement is often manifested. This disease is said to be caused by the disorder of a dopaminergic transmission system caused by the deficiency of catecholamines, in particular, DA.

For example, the DA deficiency has also been known to be one of causes of a psychosis accompanied by the reduction in spontaneous movement.

For such diseases caused by the DA deficiency, agents such as amantadine for accelerating the release of DA toward a nerve ending, agents such as biperiden for recovering the collapsed balance between a DA system and an acetylcholine system, which may be caused by antagonizing acetylcholine, and agents such as bromocriptine for binding to a DA receptor to manifest DA-like action so as to supply the deficiency of DA have been already marketed for use. However, while these agents are able to relieve the condition of a patient to some extent, neither of them are able to completely cure the condition. In addition, they have side effects such as vertigo and headache to a considerable extent and hence have been not fully satisfactory.

It is accordingly an object of the present invention to provide a neurergic agent which does not produce any side effect, is safe and has potent activities of inhibiting DA re-uptake.

With the foregoing circumstances in view, the present inventors have carried out an extensive investigation. As a result, it has been found that a compound represented by the general formula (1), which will be described subsequently, is safe and has an excellent effect of inhibiting DA re-uptake, thus leading to completion of the present invention.

DISCLOSURE OF THE INVENTION

The present invention is related to a DA re-uptake inhibitor comprising a compound represented by the following general formula (1) or a physiologically acceptable salt thereof as an active ingredient:

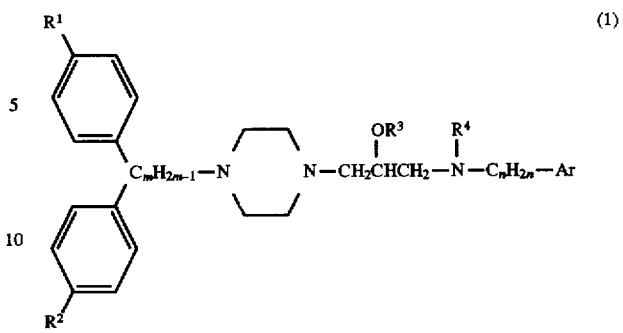

wherein $R^1$ and $R^2$ may be identical with or different from each other and mean individually a hydrogen or halogen atom, $R^3$ denotes a hydrogen atom, or an alkyl or acyl group, $R^4$ represents a hydrogen atom, or an alkyl, acyl, alkylsulfonyl or optionally esterified carboxyl group, Ar means a phenyl or nitrogen-containing monocyclic heteroaromatic group which may have 1 to 3 substituents selected from halogen atoms, and alkyl, alkoxy, nitro, amino, alkylamino and hydroxyl groups, m stands for a number of 1 to 5, and n stands for a number of 0 to 5.

The present invention is also related to a therapeutic agent for Parkinson's syndrome comprising the compound represented by the general formula (1) or the physiologically acceptable salt thereof as an active ingredient.

BEST MODE FOR CARRYING OUT THE INVENTION

In the compound useful in the practice of the present invention, which is represented by the general formula (1), with respect to the groups indicated by $R^3$, $R^4$ or Ar in the formula, the alkyl group is preferably that having 1–4 carbon atoms, the acyl group is preferably an alkylcarbonyl group having 1–4 carbon atoms, the alkylsulfonyl group is preferably that having a $C_{1-4}$ alkyl group, the alkoxy group is preferably that having 1–4 carbon atoms, the alkylamino group is preferably that having a $C_{1-4}$ alkyl group and the nitrogen-containing monocyclic heteroaromatic group is preferably a pyridyl group. Besides, m is preferably 1–5, and n is preferably 0–4.

The compounds represented by the general formula (1), which are the active ingredients according to the present invention, are known compounds, and have been already known to have calcium antagonism (WO 92/05165).

It has been known that these compounds can be prepared with ease in accordance with, for example, the following reaction scheme (WO 92/05165).

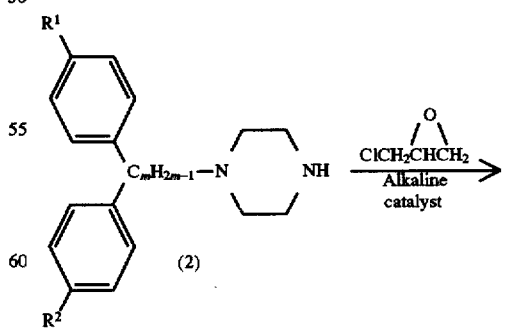

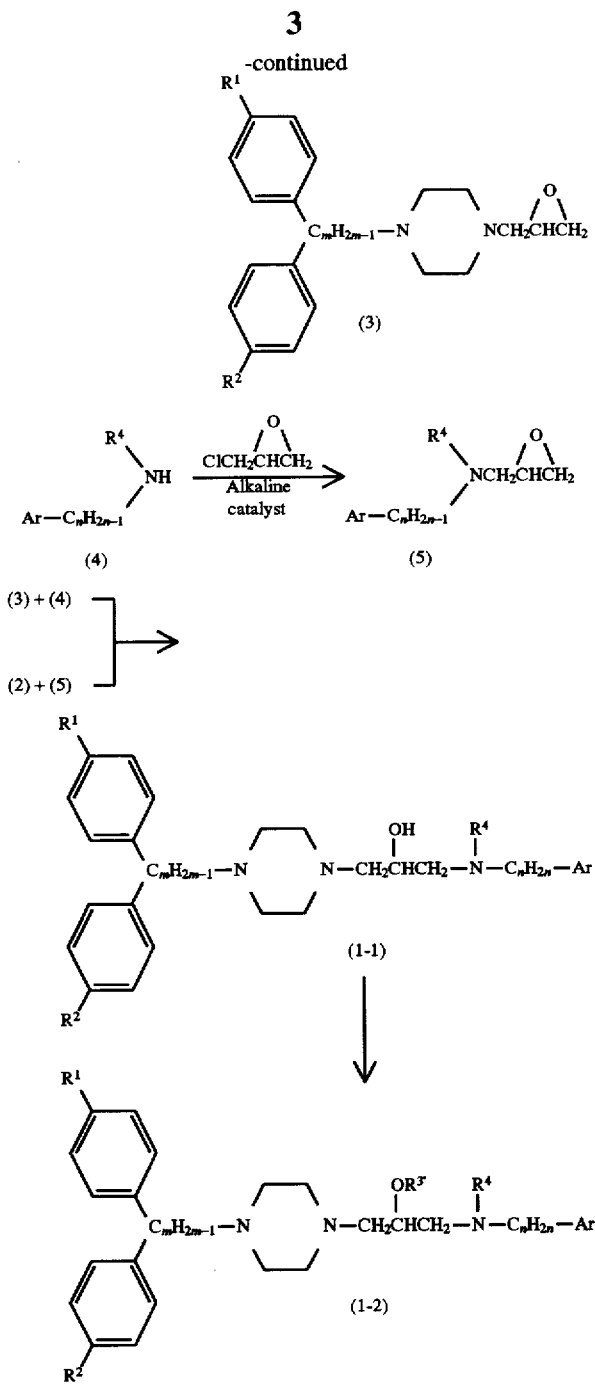

wherein $R^1$, $R^2$, $R^4$, m and n have the same meaning as defined above, and $R^{3'}$ denotes an alkyl or acyl group.

More specifically, when a diphenylpiperazine derivative (2) is reacted with epichlorohydrin in the presence of an alkaline catalyst to form an epoxide (3), and the epoxy ring of this compound is opened with an amine (4), a compound (1-1) in which $R^3$ in the compound (1) is a hydrogen atom is obtained. Besides, when a compound (4) is reacted with epichlorohydrin in the presence of an alkaline catalyst to form an epoxide (5), and the epoxy ring of this compound is opened with the compound (2), the compound (1-1) is also obtained. Furthermore, when the compound (1-1) is reacted with an alkyl halide, acyl halide or acid anhydride in the presence of an alkaline catalyst, a compound (1-2) in which $R^3$ in the compound represented by the general formula (1) is an alkyl or acyl can be obtained.

The properties of these compounds vary according to the kinds and number of the substituents. They are colorless or pale yellow liquid, amorphous or solid. With respect to their solubility, they are generally hardly soluble in water, but easily soluble in organic solvents such as methanol, chloroform and benzene. These compounds can be purified in accordance with the conventional methods such as column chromatography on silica gel and recrystallization.

The compound (1) thus obtained can be converted to a salt by the conventional method such as mixing with an acid in an organic solvent. No particular limitation is imposed on the acid used in this case so far as it is physiologically permissible. Examples thereof include mineral acids such as hydrochloric acid, phosphoric acid, nitric acid and sulfuric acid, and organic acids such as citric acid, oxalic acid, acetic acid, fumaric acid, maleic acid, malonic acid and methanesulfonic acid. However, hydrochloric acid and maleic acid are preferred from the viewpoints of handling, profitability and physical properties.

With respect to the properties of the thus-obtained salt of the compound (1), it is generally white solid and tends to be improved in both water-solubility and stability compared with the compound (1) which does not form any salt with the above-mentioned acids.

As examples of specific compound names of the compound (1) which is the active ingredient according to the present invention, may be mentioned Compound 1 to Compound 25 shown in the following Tables 1-1 to 1-5.

TABLE 1-1

| PR.No. | Structure | m | n | R¹ | R² | R³ | R⁴ | Name of compound |
|---|---|---|---|---|---|---|---|---|
| Comp'd 1 | (structure) | 4 | 0 | F | F | H | H | 1-[4,4-Bis(4-fluorophenyl)-butyl]-4-(2-hydroxy-3-phenyl-aminopropyl)piperazine dihydrochloride |
| Comp'd 2 | (structure) | 1 | 0 | F | F | H | H | 1-[Bis(4-fluorophenyl)methyl]-4-(2-hydroxy-3-phenylamino-propyl)piperazine dihydrochloride |
| Comp'd 3 | (structure) | 4 | 1 | F | F | H | H | 1-[4,4-Bis(4-fluorophenyl)-butyl]-4-(2-hydroxy-3-phenyl-methylaminopropyl)piperazine dihydrochloride |

TABLE 1-1-continued
| PR.-No. | Structure | m | n | $R^1$ | $R^2$ | $R^3$ | $R^4$ | Name of compound |
|---|---|---|---|---|---|---|---|---|
| Comp'd 4 | 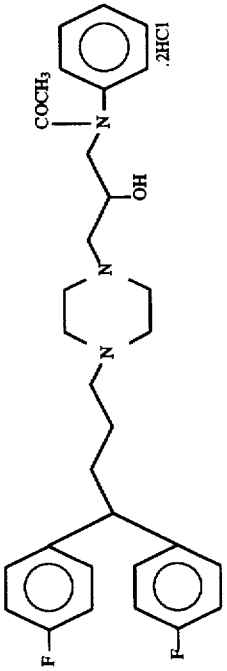 | 4 | 0 | F | F | H | $COCH_3$ | 1-[3-(N-Acetyl-N-phenylamino)-2-hydroxypropyl]-4-[4,4-bis(4-fluorophenyl)butyl]-piperazine dihydrochloride |
| Comp'd 5 | 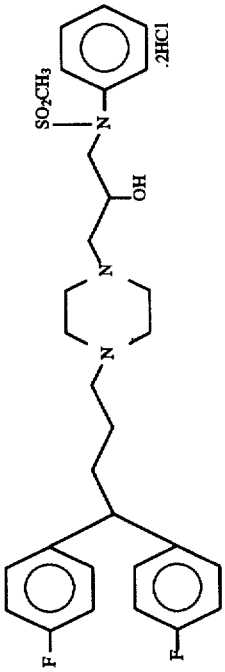 | 4 | 0 | F | F | H | $SO_2CH_3$ | 1-[4,4-Bis(4-fluorophenyl)-butyl]-4-[2-hydroxy-3-(N-methylsulfonyl-N-phenyl-amino)propyl]piperazine dihydrochloride |

TABLE 1-2

| Comp'd No. | Structure | m | n | R¹ | R² | R³ | R⁴ | Nomenclature |
|---|---|---|---|---|---|---|---|---|
| Comp'd 6 | (structure with CH₃-N-phenyl, OH, piperazine, bis(4-fluorophenyl)butyl; .2 CHCOOH/CHCOOH) | 4 | 0 | F | F | H | CH₃ | 1-[4,4-Bis(4-fluorophenyl)-butyl]-4-[2-hydroxy-3-(N-methyl-N-phenylamino)propyl]-piperazine dimaleate |
| Comp'd 7 | (structure with NH-phenyl, OCOCH₃, piperazine, bis(4-fluorophenyl)butyl; .2 CHCOOH/CHCOOH) | 4 | 0 | F | F | COCH₃ | H | 1-(2-Acetoxy-3-phenylamino-propyl)-4-[4,4-bis(4-fluoro-phenyl)butyl]piperazine dimaleate |
| Comp'd 8 | (structure with NH-phenyl, OCH₃, piperazine, bis(4-fluorophenyl)butyl; .2HCl) | 4 | 0 | F | F | CH₃ | H | 1-[4,4-Bis(4-fluorophenyl)-butyl]-4-(2-methoxy-3-phenyl-aminopropyl)piperazine dihydrochloride |

TABLE 1-2-continued

| Comp'd No. | Structure | m | n | R¹ | R² | R³ | R⁴ | Nomenclature |
|---|---|---|---|---|---|---|---|---|
| Comp'd 9 | (structure shown) ·2HCl | 4 | 0 | F | F | H | H | 1-[4,4-Bis(4-fluorophenyl)-butyl]-4-[3-(4-fluorophenyl-amino)-2-hydroxypropyl]-piperazine dihydrochloride |
| Comp'd 10 | (structure shown) ·2HCl | 4 | 0 | F | F | H | H | 1-[4,4-Bis(4-fluorophenyl)-butyl]-4-[3-(4-chlorophenyl-amino)-2-hydroxypropyl]-piperazine dihydrochloride |

TABLE 1-3

| Comp'd No. | Structure | m | n | R¹ | R² | R³ | R⁴ | Nomenclature |
|---|---|---|---|---|---|---|---|---|
| Comp'd 11 | 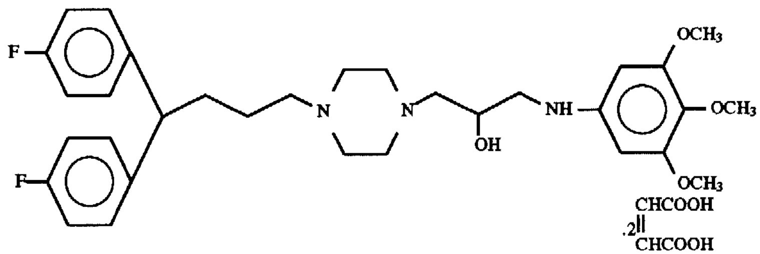 | 4 | 0 | F | F | H | H | 1-[4,4-Bis(4-fluorophenyl)-butyl]-4-[2-hydroxy-3-(3,4,5-trimethoxyphenylamino)propyl]-piperazine dimaleate |
| Comp'd 12 | 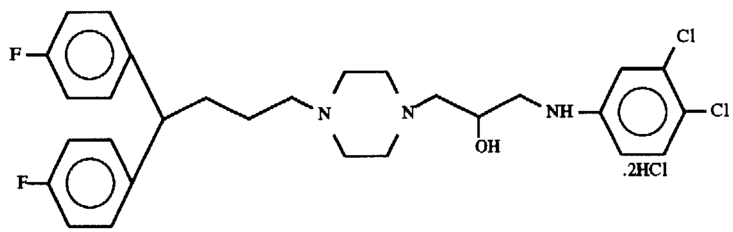 | 4 | 0 | F | F | H | H | 1-[4,4-Bis(4-fluorophenyl)-butyl]-4-[3-(3,4-dichloro-phenylamino)-2-hydroxy-propyl]piperazine dihydrochloride |
| Comp'd 13 | 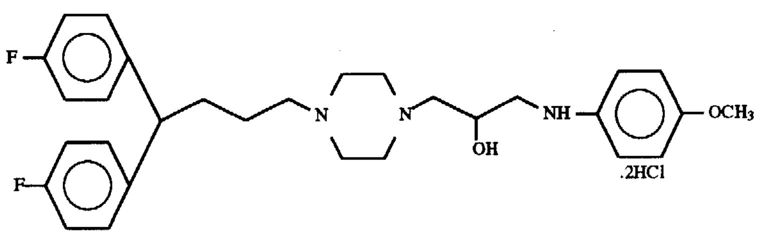 | 4 | 0 | F | F | H | H | 1-[4,4-Bis(4-fluorophenyl)-butyl]-4-(2-hydroxy-3-(4-methoxyphenylamino)propyl]-piperazine dihydrochloride |

TABLE 1-3-continued

| Comp'd No. | Structure | m | n | R¹ | R² | R³ | R⁴ | Nomenclature |
|---|---|---|---|---|---|---|---|---|
| Comp'd 14 | (structure with two 4-fluorophenyl groups, piperazine, hydroxypropyl linker, NH-(4-methylphenyl), ·2HCl) | 4 | 0 | F | F | H | H | 1-[4,4-Bis(4-fluorophenyl)-butyl]-4-[2-hydroxy-3-(4-methylphenylamino)propyl]-piperazine dihydrochloride |
| Comp'd 15 | (structure with two 4-fluorophenyl groups, piperazine, hydroxypropyl linker with * chiral center, NH-phenyl, (−), ·2HCl) | 4 | 0 | F | F | H | H | (−)-1-[4,4-Bis(4-fluorophenyl)butyl]-4-(2-hydroxy-3-phenylaminopropyl)piperazine dihydrochloride |

TABLE 1-4

| Comp'd No. | Structure | m | n | R¹ | R² | R³ | R⁴ | Nomenclature |
|---|---|---|---|---|---|---|---|---|
| Comp'd 16 | 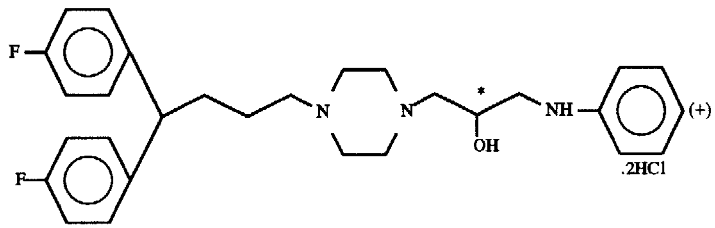 | 4 | 0 | F | F | H | H | (+)-1-[4,4-Bis(4-fluorophenyl)butyl]-4-(2-hydroxy-3-phenylaminopropyl)piperazine dihydrochloride |
| Comp'd 17 | 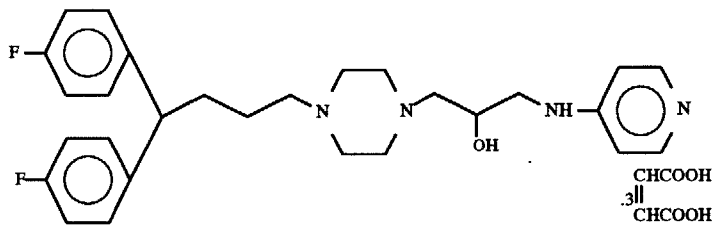 | 4 | 0 | F | F | H | H | 1-[4,4-Bis(4-fluorophenyl)-butyl]-4-[2-hydroxy-3-(4-pyridylamino)propyl]-piperazine trimaleate |
| Comp'd 18 | 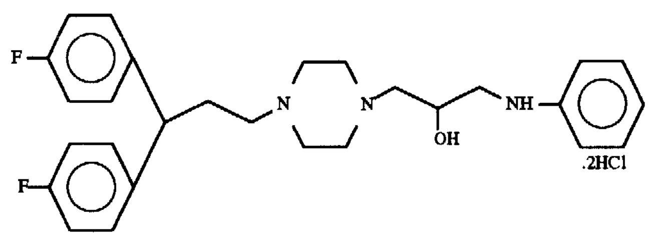 | 3 | 0 | F | F | H | H | 1-[3,3-Bis(4-fluorophenyl)-propyl]-4-(2-hydroxy-3-phenylaminopropyl)piperazine dihydrochloride |

TABLE 1-4-continued

| Comp'd No. | Structure | m | n | R¹ | R² | R³ | R⁴ | Nomenclature |
|---|---|---|---|---|---|---|---|---|
| Comp'd 19 | (structure with two 4-fluorophenyl groups, piperazine, 2-hydroxy-propyl, NH-phenyl, .2HCl) | 2 | 0 | H | H | H | H | 1-(2,2-Diphenylethyl)-4-(2-hydroxy-3-phenylamino-propyl)piperazine dihydrochloride |
| Comp'd 20 | (structure with two phenyl groups with F, piperazine, 2-hydroxy-propyl, NH-phenyl-NO₂, .2HCl) | 4 | 0 | F | F | H | H | 1-[4,4-Bis(4-fluorophenyl)-butyl]-4-[2-hydroxy-3-(4-nitrophenylamino)propyl]-piperazine dihydrochloride |

TABLE 1-5

| Comp'd No. | Structure | m | n | R¹ | R² | R³ | R⁴ | Nomenclature |
|---|---|---|---|---|---|---|---|---|
| Comp'd 21 | 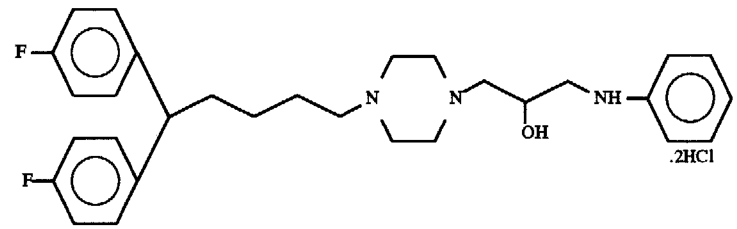 | 5 | 0 | F | F | H | H | 1-[5,5-Bis(4-fluorophenyl)-pentyl]-4-(2-hydroxy-3-phenylaminopropyl)piperazine dihydrochloride |
| Comp'd 22 | 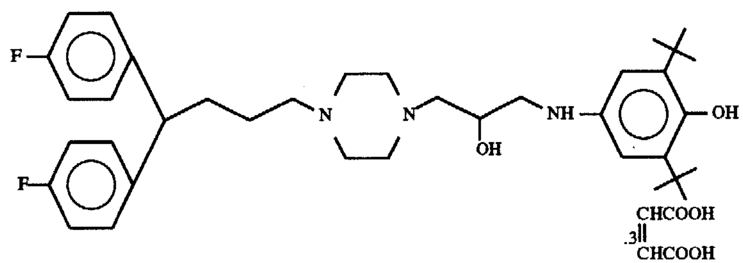 | 4 | 0 | F | F | H | H | 1-[4,4-Bis(4-fluorophenyl)-butyl]-4-[3-(3,5-di-tert-butyl-4-hydroxyphenylamino)-2-hydroxypropyl]piperazine trimaleate |
| Comp'd 23 | 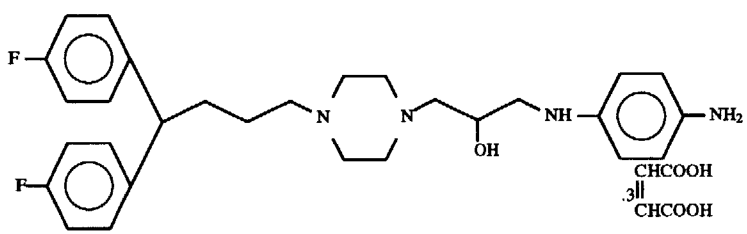 | 4 | 0 | F | F | H | H | 1-[3-(4-Aminophenylamino)-2-hydroxypropyl]-4,4-bis(4-fluorophenyl)butyl]piperazine trimaleate |

TABLE 1-5-continued
| Comp'd No. | Structure | m | n | $R^1$ | $R^2$ | $R^3$ | $R^4$ | Nomenclature |
|---|---|---|---|---|---|---|---|---|
| Comp'd 24 | 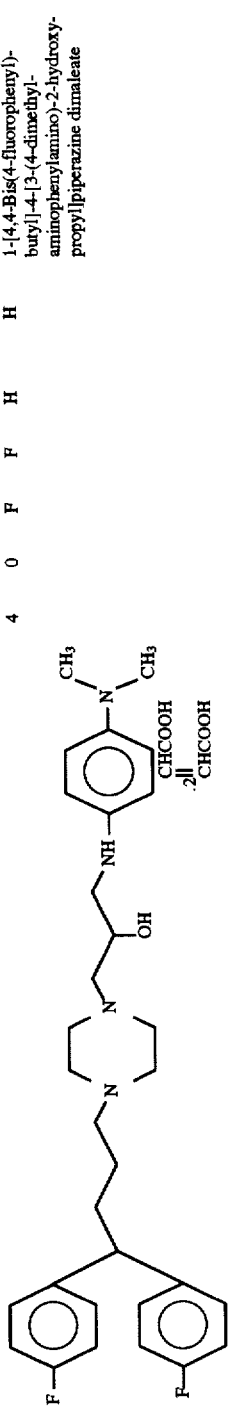 | 4 | 0 | F | F | H | H | 1-[4,4-Bis(4-fluorophenyl)-butyl]-4-[3-(4-dimethyl-aminophenyl)amino)-2-hydroxy-propyl]piperazine dimaleate |
| Comp'd 25 | 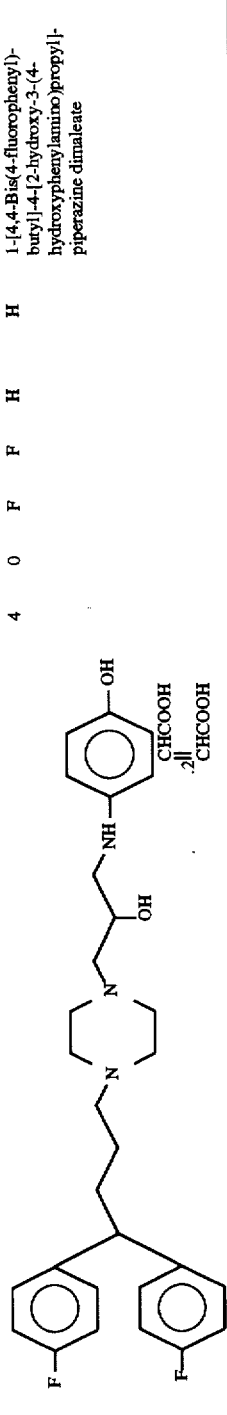 | 4 | 0 | F | F | H | H | 1-[4,4-Bis(4-fluorophenyl)-butyl]-4-[2-hydroxy-3-(4-hydroxyphenylamino)propyl]-piperazine dimaleate |

All of these compounds or salts thereof have a $LD_{50}$ value as high as at least 1000 mg/kg in mice (WO 92/05165) and hence are excellent in safety and moreover have pharmacological actions to nervous systems such as excellent DA re-uptake inhibiting action and excellent spontaneous movement-enhancing action. Therefore, they are very useful for treating diseases caused by DA deficiency, including Parkinson's syndrome.

The DA re-uptake inhibitor according to the present invention contains the compound (1) or the salt thereof as an active ingredient. Such a compound may be orally or parenterally administered by mixing it with pharmaceutical auxiliary components, for example, an excipient, binder, diluent, solubilizing and dispersing agent, etc. to prepare into any optional form such as powder, granule, tablet, capsule, solution or injection. The dose of such a preparation varies according to the age, weight, sex and condition of the patient to be dosed. However, the dose is suitably 10–1000 mg in terms of the compound per adult for the oral administration, or 1–500 mg per adult for the parenteral administration. The dose per day may be given once or in portions. As needed, the compound according to the present invention may be mixed with any other agent to administer the mixture.

EXAMPLES

The present invention will hereinafter be described in more detail by the following examples. However, this invention is not limited to these examples.

Example 1

After a cold 50 mM Tris-citrate buffer (pH 7.4, including 120 mM NaCl and 4 mM $MgCl_2$) was added to a corpus striatum taken out of a Wistar male rat aged 12–13 weeks (while keeping on ice) to homogenize the resultant mixture, the homogenate was subjected twice to centrifugation under chilling for 20 minutes at 48,000 g. The final sedimentation residue thus obtained was suspended again in the same buffer as that used above to conserve the suspension at −80° C.

After thawing this frozen suspension, the thawed suspension was diluted to one thousandth of the amount of the tissue with the same buffer as that used above. To 0.8 ml of this crude membrane sample, were added [$^3$H] GBR12935 (final concentration: 1 nM) and individual test substances and amantadine which is in clinical use at present (developing the concentration within a range of from $10^{-3}$ to $10^{-9}$M) to 1 ml in total. Each of the resulting sample mixtures was incubated at 4° C. for 80 minutes in a plastic tube. After the incubation, the mixture was filtered by means of suction on a glass filter (Whatman GP/B) soaked in a 0.1% BSA, and the filter was washed three times with 3 ml of cold 0.9% NaCl. The thus-obtained filter was placed in a vial, and 10 ml of Aquazol-2 were added to conserve the filter overnight. Thereafter, the radioactivity of the sample was measured by a liquid scintillation counter. An $IC_{50}$ value and a Hill coefficient were determined from the obtained uptake inhibition curve as to each of the test samples. The results are shown in Table 2.

TABLE 2

$IC_{50}$ values (nM) and Hill coefficents of individual agents on 1 nM [$^3$H] GBR12935 binding in rat strialal crude membrane

| Compound | $IC_{50}$ | nH | n |
|---|---|---|---|
| Amantadine | 819.29 ± 30.90 (µM) | 1.36 ± 0.08 | 4 |
| Compound 2 | 20.00 ± 3.00 | 0.66 ± 0.05 | 6 |
| Compound 9 | 4.00 ± 0.23 | 0.74 ± 0.01 | 6 |
| Compound 10 | 3.00 ± 0.32 | 0.82 ± 0.03 | 6 |
| Compound 11 | 43.00 ± 5.32 | 0.79 ± 0.04 | 6 |
| Compound 12 | 12.00 ± 0.72 | 0.74 ± 0.03 | 6 |
| Compound 13 | 3.00 ± 0.16 | 0.52 ± 0.02 | 5 |
| Compound 14 | 4.00 ± 0.41 | 0.65 ± 0.03 | 6 |
| Compound 15 | 2.00 ± 0.10 | 0.72 ± 0.05 | 6 |
| Compound 16 | 2.00 ± 0.53 | 0.57 ± 0.04 | 6 |
| Compound 17 | 34.00 ± 2.00 | 0.74 ± 0.04 | 6 |
| Compound 18 | 7.00 ± 0.65 | 0.67 ± 0.04 | 6 |
| Compound 19 | 28.00 ± 2.00 | 0.76 ± 0.02 | 6 |
| Compound 20 | 8.00 ± 0.50 | 0.69 ± 0.04 | 6 |
| Compound 21 | 6.00 ± 0.32 | 0.89 ± 0.07 | 6 |
| Compound 22 | 87.00 ± 7.00 | 0.78 ± 0.07 | 6 |
| Compound 23 | 37.00 ± 9.00 | 0.64 ± 0.09 | 6 |
| Compound 24 | 109.00 ± 19.00 | 0.94 ± 0.10 | 6 |
| Compound 25 | 10.00 ± 3.00 | 0.63 ± 0.09 | 6 |

Example 2

Investigation as to inhibition of [$^3$H]-DA re-uptake

Corpus striatum samples of Sprague-Dawley rats (SD rats) were used to investigate the inhibition of [$^3$H]-DA re-uptake.

More specifically, after an SD rat (aged 8 weeks, male) was decapitated, its corpus striatum was taken out while keeping on ice. A Krebs-Henseleit buffer in an amount ten times of the corpus striatum was added thereto to homogenize the resultant mixture by means of a Teflon homogenizer, thereby obtaining a homogenate. To this homogenate, were added nialamide as a monoamine oxidase inhibitor, ascorbic acid as an antioxidant and a test agent to preincubate the resulting mixture at 37° C. for 5 minutes. Thereafter, [$^3$H]-DA was added to conduct a reaction for 2 minutes, and cocaine was added to stop the reaction. After the reaction mixture was filtered by means of a cell harvester in which a filter had been set, the filter was washed twice with physiological saline. The washed filter was placed in a vial, and 10 ml of Aquazol-2 were added to leave the filter to stand overnight. Thereafter, the radioactivity of the sample was measured by a liquid scintillation counter.

Compound 1 according to the present invention was used as a test agent. The test agent was prepared into a $10^{-2}$M solution in dimethyl sulfoxide, and the solution was diluted with a Krebs-Henseleit buffer before its use. With the concentrations of the test substances, 11 points were selected within a range of from $10^{-10}$M to $10^{-5}$M to plot the concentration versus the amount of DA re-uptake. From this plot, an $IC_{50}$ value was determined. The $IC_{50}$ value was 6.79 nM, and the amounts of DA re-uptake and the concentrations of the agent were as shown in Table 3.

TABLE 3

| Concentration of test substance −log (mol) | Dimethyl sulfoxide | Compound 1 |
|---|---|---|
| 10 | 105% | 92% |
| 9 | 106% | 80% |
| 8 | 115% | 38% |

TABLE 3-continued

| Concentration of test substance −log (mol) | Dimethyl sulfoxide | Compound 1 |
|---|---|---|
| 7 | 119% | 2% |
| 6.5 | 110% | 0% |
| 6 | 123% | 0% |

It was apparent from the above results that Compound 1 according to the present invention has potent activities of inhibiting DA re-uptake.

Example 3
Determination of quantity of spontaneous movement

Wistar rats (male) aged 7 weeks were used to confirm the effect of Compound 1 on spontaneous movement. More specifically, after a solution or dispersion of a test agent in physiological saline was intraperitoneally administered to the rats were observed for 3 hours by a video camera to determine the quantity of movement. The number of times of traversing sections of a floor and the number of times of rising were used as indices of the quantity of movement. The test agent was used in doses of from 0.1 mmol/kg down to 0.01 mmol/kg. Besides, physiological saline alone was used as a control. The results are shown in Table 4. It is apparent that the hydrochloride of Compound 1 enhances the quantity of the spontaneous movement to a marked extent.

TABLE 4

| | Concentration (mmol/kg) | Number of times of traversing (times) | Number of times of rising (times) |
|---|---|---|---|
| Compound 1 | 0.01 | 253 | 69 |
| Compound 1 | 0.03 | 267 | 156 |
| Compound 1 | 0.1 | 287 | 121 |
| Control | | 20 | 2 |

INDUSTRIAL APPLICABILITY

The DA re-uptake inhibitors according to the present invention do not produce any side effect, are safe, have potent activities of inhibiting DA re-uptake and enhancing the quantity of spontaneous movement, and are very useful for treating Parkinson's syndrome considered to be a disease caused by DA deficiency.

What is claimed is:

1. A method for inhibiting dopamine re-uptake in a mammal comprising administering an effective amount of a compound represented by the following formula (1) or a physiologically acceptable salt thereof:

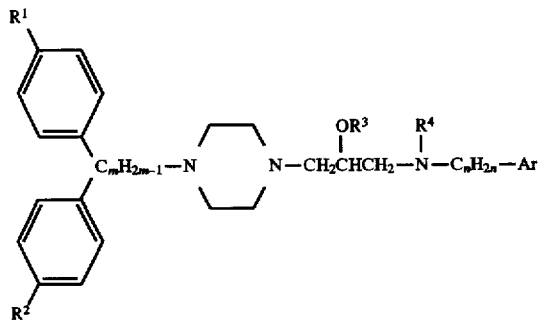

(1)

wherein $R^1$ and $R^2$ may be identical with or different from each other and mean individually a hydrogen or halogen atom, $R^3$ denotes a hydrogen atom, or an alkyl or acyl group, $R^4$ represents a hydrogen atom, or an alkyl, acyl, alkylsulfonyl or optionally esterified carboxyl group, Ar means a phenyl or nitrogen-containing monocyclic heteroaromatic group which may have 1 to 3 substituents selected from halogen atoms, or alkyl, alkoxy, nitro, amino, alkylamino or hydroxyl groups, m stands for a number of 1 to 5, and n stands for a number of 0 to 5.

2. The method of claim 1, comprising administering a dopamine re-uptake inhibitor compound of formula (1), wherein $R^3$ is an alkyl group having 1–4 carbon atoms or an alkylcarbonyl group having 1–4 carbon atoms;

$R^4$ is an alkyl group having 1–4 carbon atoms, an alkylcarbonyl group having 1–4 carbon atoms, or an alkylsulfonyl group containing a $C_{1-4}$ alkyl group;

Ar is a phenyl group or a nitrogen-containing monocyclic heteroaromatic group, having 1 to 3 substituents selected from an alkyl group having 1–4 carbon atoms, an alkoxy group having 1–4 carbon atoms, or alkylamino having a $C_{1-4}$ alkyl group, or Ar is a pyridyl group;

and n stands for a number of 0 to 4.

3. The method of claim 1, comprising administering one or more compounds selected from the group consisting of 1-[4,4-bis(4-fluorophenyl)butyl]-4-(2-hydroxy-3-phenylaminopropyl)-piperazine, 1-[bis(4-fluorophenyl) methyl]-4-(2-hydroxy-3-phenylaminopropyl)piperazine, 1-[4,4-bis(4-fluorophenyl)butyl]-4-(2-hydroxy-3-phenylmethylaminopropyl)piperazine, 1-[3-(N-acetyl-N-phenylamino)-2-hydroxypropyl]-4-[4,4-bis(4-fluorophenyl)butyl]piperazine, 1-[4,4-bis(4-fluorophenyl)butyl]-4-[2-hydroxy-3-(N-methylsulfonyl-N-phenylamino)propyl]piperazine, 1-[4,4-bis(4-fluorophenyl)butyl]-4-[2-hydroxy-3-(N-methyl-N-phenylamino)propyl]piperazine, 1-(2-acetoxy-3-phenylaminopropyl)-4-[4,4-bis(4-fluorophenyl)butyl]piperazine, 1-[4,4-bis(4-fluorophenyl)butyl]-4-(2-methoxy-3-phenylaminopropyl)piperazine, 1-[4,4-bis(4-fluorophenyl)butyl]-4-[3-(4-fluorophenylamino)-2-hydroxypropyl]piperazine, 1-[4,4-bis(4-fluorophenyl)butyl]-4-[3-(4-chlorophenylamino)-2-hydroxypropyl]piperazine, 1-[4,4-bis(4-fluorophenyl)butyl]-4-[2-hydroxy-3-(3,4,5-trimethoxyphenylamino)propyl]piperazine, 1-[4,4-bis(4-fluorophenyl)butyl]-4-[3-(3,4-dichlorophenylamino)-2-hydroxypropyl]piperazine, 1-[4,4-bis(4-fluorophenyl)butyl]-4-[2-hydroxy-3-(4-methoxyphenylamino)propyl]piperazine, 1-[4,4-bis(4-fluorophenyl)butyl]-4-[2-hydroxy-3-(4-methylphenylamino)propyl]piperazine, 1-[4,4-bis(4-fluorophenyl)butyl]-4-[2-hydroxy-3-(4-pyridylamino)propyl]piperazine, 1-[3,3-bis(4-fluorophenyl)propyl]-4-(2-hydroxy-3-phenylaminopropyl)piperazine, 1-(2,2-diphenylethyl)-4-(2-hydroxy-3-phenylaminopropyl)piperazine, 1-[4,4-bis(4-fluorophenyl)butyl]-4-[2-hydroxy-3-(4-nitrophenylamino)propyl]piperazine, 1-[5,5-bis(4-fluorophenyl)pentyl]-4-(2-hydroxy-3-phenylaminopropyl)piperazine, 1-[4,4-bis(4-fluorophenyl)butyl]-4-[3-(3,5-di-tert-butyl-4-hydroxyphenylamino)-2-hydroxypropyl]piperazine, 1-[3-(4-aminophenylamino)-2-hydroxypropyl]-4-[4,4-bis(4-fluorophenyl)butyl]piperazine, 1-(4,4-bis(4-fluorophenyl)butyl]-4-[3-(4-dimethylaminophenylamino)-2-hydroxypropyl]piperazine and 1-[4,4-bis(4-fluorophenyl) butyl]-4-[2-hydroxy-3-(4-hydroxyphenylamino)propyl] piperazine.

4. The method of claim 1, comprising administering 1-[4,4-bis(4-fluorophenyl)-butyl]-4-(2-hydroxy-3-phenylaminopropyl)piperazine dihydrochloride.

5. The method of claim 1, comprising orally administering 10–1000 mg of the compound of formula (1) or a physiologically acceptable salt thereof.

6. The method of claim 1, comprising parenterally administering 1-500 mg of the compound of formula (1) or a physiologically acceptable salt thereof.

7. A method for treating a human subject suffering from Parkinson's disease, comprising administering an effective amount of a compound represented by the following formula (1) or a physiologically acceptable salt thereof:

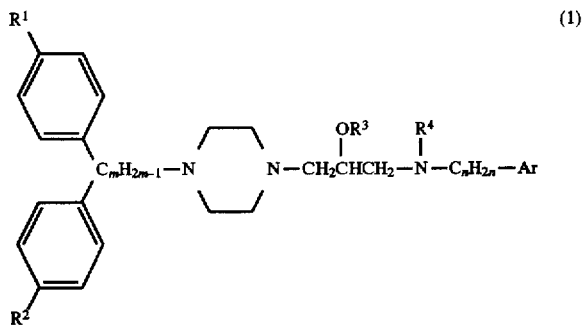

wherein $R^1$ and $R^2$ may be identical with or different from each other and mean individually a hydrogen or halogen atom, $R^3$ denotes a hydrogen atom, or an alkyl or acyl group, $R^4$ represents a hydrogen atom, or an alkyl, acyl, alkylsulfonyl or optionally esterified carboxyl group, Ar means a phenyl or nitrogen-containing monocyclic heteroaromatic group which may have 1 to 3 substituents selected from halogen atoms, and alkyl, alkoxy, nitro, amino, alkylamino and hydroxyl groups, m stands for a number of 1 to 5, and n stands for a number of 0 to 5.

8. The method of claim 7, comprising administering a compound of formula (1), wherein $R^3$ is an alkyl group having 1–4 carbon atoms or an alkylcarbonyl group having 1–4 carbon atoms;

$R^4$ is an alkyl group having 1–4 carbon atoms, an alkylcarbonyl group having 1–4 carbon atoms, or an alkylsulfonyl group containing a $C_{1-4}$ alkyl group;

Ar is a phenyl group or a nitrogen-containing monocyclic heteroaromatic group, having 1 to 3 substituents selected from an alkyl group having 1–4 carbon atoms, an alkoxy group having 1–4 carbon atoms, or alkylamino having a $C_{1-4}$ alkyl group, or Ar is a pyridyl group;

and n stands for a number of 0 to 4.

9. The method of claim 7, comprising administering one or more compounds selected from the group consisting of 1-[4,4-bis(4-fluorophenyl)butyl]-4-(2-hydroxy-3-phenylaminopropyl)piperazine, 1-[bis(4-fluorophenyl) methyl]-4-(2-hydroxy-3-phenylaminopropyl)piperazine, 1-[4,4-bis(4-fluorophenyl)butyl]-4-(2-hydroxy-3-phenylmethylaminopropyl)piperazine, 1-[3-(N-acetyl-N-phenylamino)-2-hydroxypropyl]-4-[4,4-bis(4-fluorophenyl) butyl]piperazine, 1-[4,4-bis(4-fluorophenyl)butyl]-4-[2-hydroxy-3-(N-methylsulfonyl-N-phenylamino)propyl] piperazine, 1-[4,4-bis(4-fluorophenyl)butyl]-4-[2-hydroxy-3-(N-methyl-N-phenylamino)propyl]-piperazine, 1-(2-acetoxy-3-phenylaminopropyl)-4-(4,4-bis(4-fluorophenyl) butyl]piperazine, 1-[4,4-bis(4-fluorophenyl)butyl]-4-(2-methoxy-3-phenylaminopropyl)piperazine, 1-[4,4-bis(4-fluorophenyl)butyl]-4-[3-(4-fluorophenylamino)-2-hydroxypropyl]piperazine, 1-[4,4-bis(4-fluorophenyl)butyl] -4-[3-(4-chlorophenylamino)-2-hydroxypropyl]piperazine, 1-[4,4-bis(4-fluorophenyl)butyl]-4-[2-hydroxy-3-(3,4,5-trimethoxyphenylamino)propyl]piperazine, 1-[4,4-bis(4-fluorophenyl)butyl]-4-[3-(3,4-dichlorophenylamino)-2-hydroxypropyl]piperazine, 1-[4,4-bis(4-fluorophenyl)butyl] -4-[2-hydroxy-3-(4-methoxyphenylamino)propyl] piperazine, 1-[4,4-bis(4-fluorophenyl)butyl]-4-[2-hydroxy-3-(4-methylphenylamino)propyl]piperazine, 1-[4,4-bis(4-fluorophenyl)butyl]-4-[2-hydroxy-3-(4-pyridylamino) propyl]piperazine, 1-[3,3-bis(4-fluorophenyl)propyl]-4-(2-hydroxy-3-phenylaminopropyl)piperazine, 1-(2,2-diphenylethyl)-4-(2-hydroxy-3-phenylaminopropyl) piperazine, 1-[4,4-bis(4-fluorophenyl)butyl]-4-[2-hydroxy-3-(4-nitrophenylamino)propyl]piperazine, 1-[5,5-bis(4-fluorophenyl)pentyl]-4-(2-hydroxy-3-phenylaminopropyl) piperazine, 1-[4,4-bis(4-fluorophenyl)butyl]-4-[3-(3,5-di-tert-butyl-4-hydroxyphenylamino)-2-hydroxypropyl] piperazine, 1-[3-(4-aminophenylamino)-2-hydroxypropyl]-4-[4,4-bis(4-fluorophenyl)butyl]piperazine, 1-[4,4-bis(4-fluorophenyl)butyl]-4-[3-(4-dimethylaminophenylamino)-2-hydroxypropyl]piperazine and 1-[4,4-bis(4-fluorophenyl) butyl]-4-[2-hydroxy-3-(4-hydroxyphenylamino)propyl]-piperazine.

10. The method of claim 7, comprising administering 1-[4,4-bis(4-fluorophenyl)-butyl]-4-(2-hydroxy-3-phenylaminopropyl)piperazine dihydrochloride.

* * * * *